US00PP35032P2

(12) United States Plant Patent
Mathey

(10) Patent No.: US PP35,032 P2
(45) Date of Patent: Mar. 14, 2023

(54) ***SPIRAEA* PLANT NAMED 'SMNSJSA'**

(50) Latin Name: *Spiraea japonica*
Varietal Denomination: SMNSJSA

(71) Applicant: Megan M. Mathey, Holland, MI (US)

(72) Inventor: Megan M. Mathey, Holland, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 17/953,084

(22) Filed: Sep. 26, 2022

(51) Int. Cl.
*A01H 5/02* (2018.01)
*A01H 6/74* (2018.01)

(52) U.S. Cl.
USPC ..... Plt./226
CPC ..... *A01H 6/74* (2018.05)

(58) Field of Classification Search
USPC ..... Plt./226
CPC ..... A01H 6/74; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Spiraea* plant named 'SMNSJSA', characterized by its compact, upright, outwardly spreading and mounding plant habit; vigorous growth habit and rapid growth rate; freely branching habit; dense and bushy habit; leaves that are initially reddish orange in color, becoming bright greenish yellow and eventually darker yellow green with development; inflorescences with numerous bright purplish red-colored flowers; and good garden performance.

4 Drawing Sheets

Figure 1:
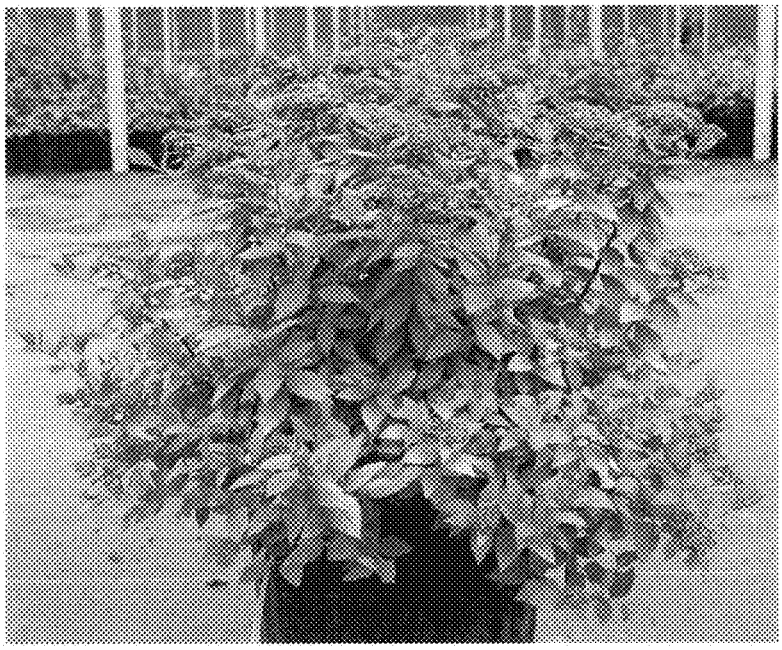

Botanical designation: *Spiraea japonica.*
Cultivar denomination: 'SMNSJSA'.

BACKGROUND OF THE INVENTION

The present invention relates to a new and distinct cultivar of *Spiraea* plant, botanically known as *Spiraea japonica*, commonly known as Japanese *Spiraea* and hereinafter referred to by the name 'SMNSJSA'.

The new *Spiraea* plant is a product of a planned breeding program conducted by the Inventor in Grand Haven, Mich. The objective of the breeding program is to develop new compact and mounding *Spiraea* plants with attractive leaves and numerous flowers.

The new *Spiraea* plant originated from an open-pollination in 2015 of an unnamed proprietary selection of *Spiraea japonica*, not patented, as the female, or seed, parent with an unknown selection of *Spiraea japonica*, as the male, or pollen, parent. The new *Spiraea* plant was discovered and selected by the Inventor in 2018 as a single flowering plant within the progeny of the stated open-pollination in a controlled environment in Grand Haven, Mich.

Asexual reproduction of the new *Spiraea* plant by softwood cuttings in a controlled greenhouse environment in Grand Haven, Mich. since 2018 has shown that the unique features of this new *Spiraea* plant are stable and reproduced true to type in successive generations of asexual reproduction.

SUMMARY OF THE INVENTION

Plants of the new *Spiraea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNSJSA'. These characteristics in combination distinguish 'SMNSJSA' as a new and distinct *Spiraea* plant:

1. Compact, upright, outwardly spreading and mounding plant habit.
2. Vigorous growth habit and rapid growth rate.
3. Freely branching habit; dense and bushy habit.
4. Leaves that are initially reddish orange in color, becoming bright greenish yellow and eventually darker yellow green with development.
5. Inflorescences with numerous bright purplish red-colored flowers.
6. Good garden performance.

Plants of the new *Spiraea* can be compared to plants of the female parent selection. Plants of the new *Spiraea* differ primarily from plants of the female parent selection in the following characteristics:

1. Leaves of plants of the new *Spiraea* are more vibrant in color than plants of the female parent selection.
2. Flowers of plants of the new *Spiraea* are darker purplish red in color than flowers of plants of the female parent selection.

Plants of the new *Spiraea* can be compared to plants of the *Spiraea japonica* 'NCSX1', disclosed in U.S. Plant Pat. No. 28,313. Plants of the new *Spiraea* differ from plants of 'NCSX1' in the following characteristics:

1. Plants of the new *Spiraea* have narrower leaves than plants of 'NCSX1'.
2. Fully expanded leaves of plants of the new *Spiraea* are yellow green in color whereas fully expanded leaves of plants of 'NCSX1' are bright yellow in color.
3. Flowers of plants of the new *Spiraea* are darker purplish red than flowers of plants of 'NCSX1'.

BRIEF DESCRIPTION OF THE PHOTOGRAPHS

The accompanying colored photographs illustrate the overall appearance of the new *Spiraea* plant showing the colors as true as it is reasonably possible to obtain in colored reproductions of this type. Colors in the photographs may differ slightly from the color values cited in the detailed botanical description which accurately describe the colors of the new *Spiraea* plant.

The photograph on the first sheet (FIG. 1) is a side perspective view of a typical plant of 'SMNSJSA' grown in a container.

Figure 2:
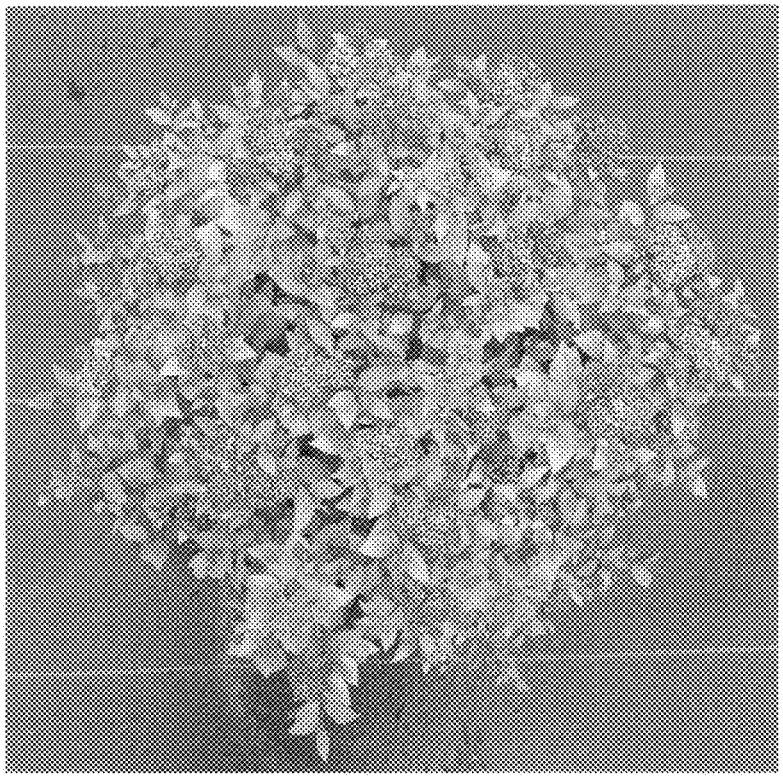

The photograph on the second sheet (FIG. 2) is a top perspective view of a typical plant of 'SMNSJSA' grown in a container.

Figure 3:
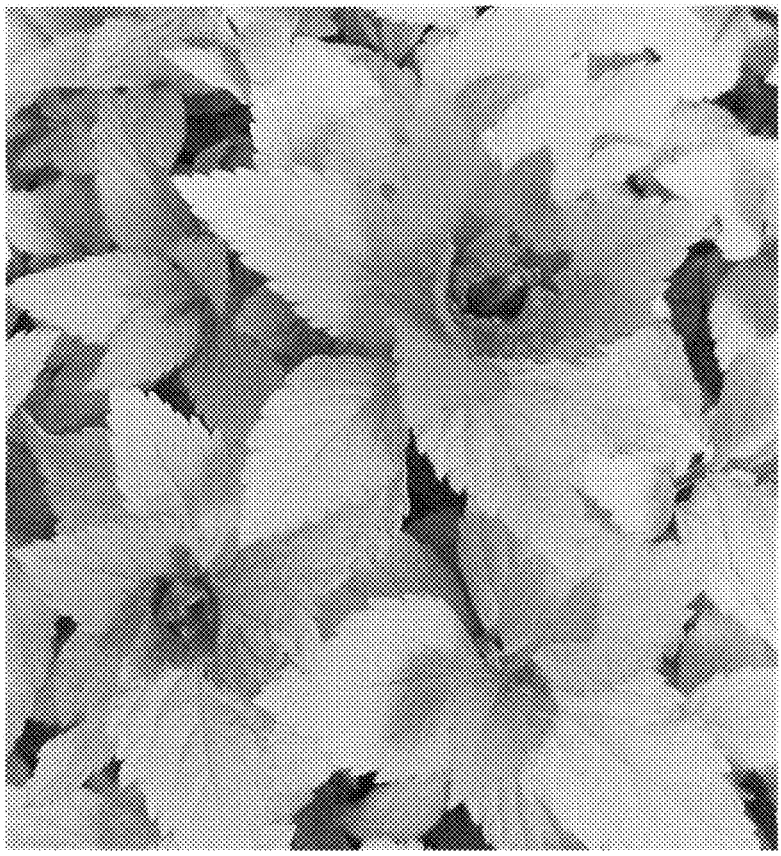

The photograph on the third sheet (FIG. 3) is a close-up view of typical developing leaves of 'SMNSJSA'.

Figure 4:
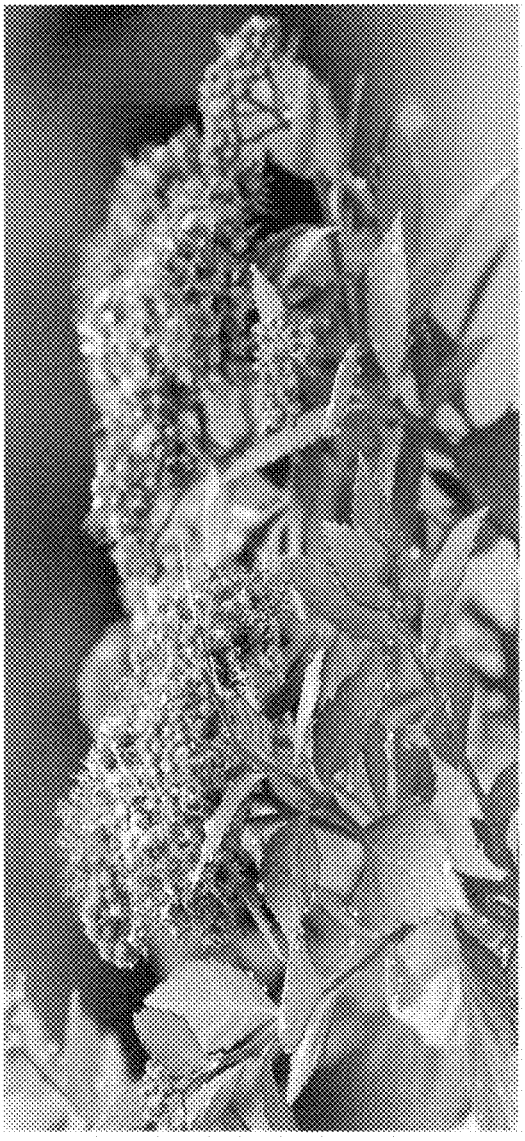

The photograph on the fourth sheet (FIG. 4) is a close-up view of typical inflorescences of 'SMNSJSA'.

DETAILED BOTANICAL DESCRIPTION

The aforementioned photographs and following observations and measurements describe plants grown during the spring and early summer in three-gallon containers in a polyethylene-covered greenhouse in Grand Haven, Mich. and under cultural practices typical of commercial *Spiraea* production. During the production of the plants, day temperatures ranged from 18° C. to 27° C. and night temperatures ranged from ranged from 5° C. to 10° C. Plants were three years old when the photographs and detailed description were taken. In the following description, color references are made to The Royal Horticultural Society Colour Chart, 2015 Edition, except where general terms of ordinary dictionary significance are used.

Botanical classification: *Spiraea japonica* 'SMNSJSA'.

Parentage:

- *Female, or seed, parent*.—Unnamed proprietary selection of *Spiraea japonica*, not patented.
- *Male, or pollen, parent*.—Unknown selection of *Spiraea japonica*, not patented.

Propagation:

- *Type*.—By softwood cuttings.
- *Time to initiate roots, summer*.—About three weeks at temperatures about 18° C. to 27° C.
- *Time to produce a rooted young plant, summer*.—About ten weeks at temperatures about 18° C. to 27° C.
- *Root description*.—Medium in thickness, fibrous; typically white in color, actual color of the roots is dependent on substrate composition, water quality, fertilizer, substrate temperature and physiological age of roots.
- *Rooting habit*.—Freely branching; dense.

Plant description:

- *Plant form and growth habit*.—Perennial shrub; compact, upright, outwardly spreading and mounding plant habit; vigorous growth habit and rapid growth rate.
- *Branching habit*.—Freely branching habit with about 30 lateral branches developing per plant; pinching (removal of terminal apices) will enhance lateral branch development; dense and bushy habit.
- *Plant height*.—About 50 cm.
- *Plant diameter* (*area of spread*).—About 65 cm.

Lateral branch description:

- *Length*.—About 40 cm.
- *Diameter*.—About 3 mm.
- *Internode length*.—About 1.5 cm.
- *Strength*.—Strong.
- *Aspect*.—About 30° to 80° from vertical.
- *Texture, developing*.—Slightly pubescent.
- *Texture, developed*.—Smooth, glabrous.
- *Color, developing*.—Close to 144C.
- *Color, developed*.—Close to 165A.

Leaf description:

- *Arrangement*.—Alternate; simple.
- *Length*.—About 4.5 cm.
- *Width*.—About 2 cm.
- *Shape*.—Lanceolate.
- *Apex*.—Acute.
- *Base*.—Attenuate.
- *Margin*.—Serrate.
- *Texture, upper surface*.—Smooth, glabrous.
- *Texture, lower surface*.—Glabrous, prominent venation.
- *Venation pattern*.—Pinnate.
- *Color*.—Developing leaves, upper and lower surfaces: Close to 173A and 173B becoming closer to 151D with development; venation, close to 174B. Fully expanded leaves, upper surface: Close to between 176B and 177A becoming closer to 166B and eventually, close to 144A with development; venation, close to 144C. Fully expanded leaves, lower surface: Close to 177B becoming closer to 138B with development; venation, close to 144C.
- *Petioles*.—Length: About 2 mm. Diameter: About 1 mm. Texture, upper and lower surfaces: Slightly pubescent. Color, developing, upper and lower surfaces: Close to 174B. Color, fully expanded, upper and lower surfaces: Close to 144C.

Flower description:

- *Flower appearance and arrangement*.—Single rotate flowers arranged in terminal corymbs; freely flowering habit with usually about 150 to 200 flowers per inflorescence; flowers face upright to slightly outwardly depending on position on inflorescence.
- *Natural flowering season*.—Continuous flowering from late spring through the summer (May through July) in Michigan; flowers not persistent.
- *Fragrance*.—Slightly fragrant, sweet.
- *Inflorescence height*.—About 1.5 cm.
- *Inflorescence diameter*.—About 5 cm.
- *Flower diameter*.—About 5 mm.
- *Flower depth*.—About 3 mm.
- *Flower buds*.—Length: About 1 mm. Diameter: About 1 mm. Shape: Orbicular. Color: Close to 182B.
- *Petals*.—Quantity and arrangement: Five in a single whorl. Length: About 2 mm. Width: About 2 mm. Shape: Orbicular. Apex: Obtuse. Base: Obtuse. Margin: Entire. Texture, upper and lower surfaces: Smooth, glabrous. Color: When opening and fully opened, upper surface: Close to 71A. When opening and fully opened, lower surface: Close to 77C and towards the margins, close to 71A.
- *Sepals*.—Quantity and arrangement: Five in a single whorl; fused at the base. Length: About 1 mm. Width: About 1 mm. Shape: Deltoid. Apex: Acute. Margin: Entire. Texture, upper and lower surfaces: Smooth, glabrous. Color: When opening and fully opened, upper surface: Close to 73D. When opening and fully opened, lower surface: Close to 73D.

*Peduncles*.—Length: About 2 cm. Diameter: About 1 mm. Strength: Strong. Aspect: About 45° from lateral branch axis. Texture: Slightly pubescent. Color: Close to 145B.

*Pedicels*.—Length: About 1 cm. Diameter: About 1 mm. Strength: Moderately strong. Aspect: About 45° from peduncle axis. Texture: Slightly pubescent. Color: Close to 145B.

*Reproductive organs*.—Androecium: Quantity per flower: About 30. Filament length: About 3 mm. Filament color: Close to 71A. Anther shape: Globose. Anther length: Less than 1 mm. Anther color: Close to 71A. Amount of pollen: Scarce. Pollen color: Close to 155D. Gynoecium: Quantity per flower: About five. Pistil length: About 2 mm. Style length: About 1.75 mm. Style color: Close to 71A. Stigma shape: Globose. Stigma color: Close to 71A.

*Seeds and fruits*.—To date, seed and fruit development has not been observed on plants of the new *Spiraea*.

Garden performance: Plants of the new *Spiraea* have been observed to have good garden performance and to tolerate rain, wind and temperatures ranging from about −31° C. to about 38° C.

Pathogen & pest resistance: To date, plants of the new *Spiraea* have not been observed to be resistant to pathogens and pests common to *Spiraea* plants.

It is claimed:

1. A new and distinct *Spiraea* plant named 'SMNSJSA' as illustrated and described.

* * * * *